(12) United States Patent
Lee et al.

(10) Patent No.: US 11,090,008 B2
(45) Date of Patent: Aug. 17, 2021

(54) NEUROPHYSIOLOGICAL MONITORING FOR PROSPECTIVE MOTION GATING IN RADIOLOGICAL IMAGING

(71) Applicant: KONINKLIJKE PHILIPS N.V., Eindhoven (NL)

(72) Inventors: Michael Chun-chieh Lee, Lexington, MA (US); Robert Manzke, Bönebüttel (DE); Yuechen Qian, Briarcliff Manor, NY (US); Eric Cohen-Solal, Ossining, NY (US)

(73) Assignee: Koninklijke Philips N.V., Eindhoven (NL)

( * ) Notice: Subject to any disclaimer, the term of this patent is extended or adjusted under 35 U.S.C. 154(b) by 235 days.

(21) Appl. No.: 14/767,691

(22) PCT Filed: Mar. 12, 2014

(86) PCT No.: PCT/IB2014/059664
§ 371 (c)(1),
(2) Date: Aug. 13, 2015

(87) PCT Pub. No.: WO2014/147519
PCT Pub. Date: Sep. 25, 2014

(65) Prior Publication Data
US 2016/0000383 A1  Jan. 7, 2016

Related U.S. Application Data

(60) Provisional application No. 61/803,505, filed on Mar. 20, 2013.

(51) Int. Cl.
*A61B 5/00* (2006.01)
*A61B 5/11* (2006.01)
(Continued)

(52) U.S. Cl.
CPC .............. *A61B 5/7292* (2013.01); *A61B 5/11* (2013.01); *A61B 5/24* (2021.01); *A61B 5/721* (2013.01);
(Continued)

(58) Field of Classification Search
CPC ..... A61B 5/7292; A61B 5/04001; A61B 5/11; A61B 5/721; A61B 5/7242; A61B 5/7267;
(Continued)

(56) References Cited

U.S. PATENT DOCUMENTS 5,271,055 A   12/1993   Hsieh et al.
6,937,696 B1   8/2005   Mostafavi
(Continued)

FOREIGN PATENT DOCUMENTS

CN   102799937 A   11/2012
JP   2005514975 A   5/2005
(Continued)

OTHER PUBLICATIONS

Lemaire, C. et al. "Impact of audio/visual systems on pediatric sedation in magnetic resonance imaging", Journal of magnetic Resonance Imaging, vol. 30, No. 3, Sep. 1, 2009, pp. 649-655.
(Continued)

*Primary Examiner* — Rex R Holmes
*Assistant Examiner* — Sana Sahand

(57) ABSTRACT

A system, method and non-transitory computer-readable storage medium for monitoring motion during medical imaging. The monitoring of the motion includes initiating an acquisition of image data, measuring physiological signals of a patient, generating a prediction signal by integrating the physiological signals, determining whether patient motion is
(Continued)

likely to occur based on the prediction signal and modifying the acquisition of image data, if it is predicted that patient motion is likely to occur.

15 Claims, 3 Drawing Sheets

(51) Int. Cl.
| | |
|---|---|
| *G16H 30/40* | (2018.01) |
| *G16H 40/63* | (2018.01) |
| *G16H 30/20* | (2018.01) |
| *G16H 50/70* | (2018.01) |
| *G01R 33/567* | (2006.01) |
| *A61B 6/00* | (2006.01) |
| *A61B 5/24* | (2021.01) |
| *G16H 20/70* | (2018.01) |
| *A61B 5/245* | (2021.01) |
| *A61B 5/318* | (2021.01) |
| *A61B 5/369* | (2021.01) |
| *A61B 5/389* | (2021.01) |

(52) U.S. Cl.
CPC .......... *A61B 5/7242* (2013.01); *A61B 5/7267* (2013.01); *A61B 5/7275* (2013.01); *A61B 6/541* (2013.01); *G01R 33/5673* (2013.01); *G16H 30/20* (2018.01); *G16H 30/40* (2018.01); *G16H 40/63* (2018.01); *G16H 50/70* (2018.01); *A61B 5/245* (2021.01); *A61B 5/318* (2021.01); *A61B 5/369* (2021.01); *A61B 5/389* (2021.01); *G16H 20/70* (2018.01)

(58) Field of Classification Search
CPC .................. A61B 5/7275; A61B 6/541; A61B 6/5258–527; G01R 33/4806; G61R 33/5673; G61R 33/567
USPC ........................................................ 600/301
See application file for complete search history.

(56) References Cited

U.S. PATENT DOCUMENTS

| | | | |
|---|---|---|---|
| 8,214,012 B2* | 7/2012 | Zuccolotto | A61B 5/0555 |
| | | | 324/306 |
| 9,232,928 B2 | 1/2016 | Mostafavi | |
| 9,535,145 B2 | 1/2017 | Demeester et al. | |
| 9,717,461 B2* | 8/2017 | Yu | A61B 5/721 |
| 2003/0007601 A1* | 1/2003 | Jaffray | A61B 6/032 |
| | | | 378/65 |
| 2005/0082491 A1 | 4/2005 | Seppi et al. | |
| 2005/0201510 A1* | 9/2005 | Mostafavi | A61B 5/7292 |
| | | | 378/8 |
| 2006/0209257 A1* | 9/2006 | Bullwinkel | A61B 3/113 |
| | | | 351/210 |
| 2007/0179534 A1* | 8/2007 | Firlik | A61B 5/16 |
| | | | 607/3 |
| 2008/0309333 A1 | 12/2008 | Stehning et al. | |
| 2010/0290683 A1* | 11/2010 | Demeester | A61B 6/037 |
| | | | 382/131 |
| 2012/0310053 A1 | 12/2012 | Henning et al. | |
| 2013/0053676 A1* | 2/2013 | Kemper | A61B 6/035 |
| | | | 600/407 |
| 2013/0245364 A1* | 9/2013 | Gillies | A61B 5/742 |
| | | | 600/28 |
| 2014/0148657 A1* | 5/2014 | Hendler | A61B 5/0476 |
| | | | 600/301 |
| 2017/0215830 A1 | 8/2017 | Henning et al. | |

FOREIGN PATENT DOCUMENTS

| | | | | |
|---|---|---|---|---|
| RU | 2504006 A | 12/2013 | | |
| WO | 03003796 A1 | 1/2003 | | |
| WO | WO-03003796 A1 * | 1/2003 | ............. | A61B 5/113 |

OTHER PUBLICATIONS

Colette Lemaire et al Impact of Audio/Visual Systems on Pediatric Sedation in Magnetic Resonance Imaging, Journal of Magnetic Resonance Imaging, 2009 p. 649-655.

* cited by examiner

NEUROPHYSIOLOGICAL MONITORING FOR PROSPECTIVE MOTION GATING IN RADIOLOGICAL IMAGING

CROSS-REFERENCE TO PRIOR APPLICATIONS

This application is the U.S. National Phase application under 35 U.S.C. § 371 of International Application No. PCT/IB2014/059664, filed on Mar. 12, 2014, which claims the benefit of U.S. Provisional Application No. 61/803,505, filed on Mar. 20, 2013. These applications are hereby incorporated by reference herein.

BACKGROUND

Acquisition of medical images for tomographic imaging such as, for example, a CT or MRI, may take place over an extended period of time (e.g., several seconds or minutes). Data is collected over a time period and reconstructed to create a final image volume. Patient motion during the imaging period, however, may result in portions of the data being corrupted since data acquired while the patient is in a different physical position cannot be combined with the remaining data. Thus, motion during the imaging period greatly complicates the image reconstruction.

Current motion correction and motion compensation algorithms are retrospective. For example, motion-corrupted data may be rejected during the final image reconstruction. It is difficult, however, to determine during the imaging how much motion-corrupted data has been acquired. Thus, final image characteristics (e.g., signal-to-noise) may vary between otherwise identical scans since different amounts of data may be used in the image reconstruction. In addition, for medical imaging processes that require ionizing radiation (e.g., CT imaging), it is desired to limit the radiation exposure to the patient and any operators near the imaging system. Acquiring corrupted data that will eventually be rejected, however, still exposes the patient to radiation without any added benefit. Devices utilizing motion compensation methods to detect motion during the acquisition itself still present the same problem, as the image data must still be acquired first.

SUMMARY

A method for monitoring motion during medical imaging. The method includes initiating an acquisition of image data, measuring physiological signals of a patient, generating a prediction signal by integrating the physiological signals, determining whether patient motion is likely to occur based on the prediction signal and modifying the acquisition of image data, if it is predicted that patient motion is likely to occur.

A system for monitoring motion during medical imaging. The system includes a monitoring system measuring physiological signals of a patient and a processor initiating an acquisition of image data, generating a prediction signal by integrating the physiological signals, determining whether patient motion is likely to occur based on the prediction signal and modifying the acquisition of image data, if it is predicted that patient motion is likely to occur.

A non-transitory computer-readable storage medium including a set of instructions executable by a processor. The set of instructions being operable to initiate an acquisition of image data, measure physiological signals of a patient, generate a prediction signal by integrating the physiological signals, determine whether patient motion is likely to occur based on the prediction signal and modify the acquisition of image data, if it is predicted that patient motion is likely to occur.

DETAILED DESCRIPTION

Figure 1:
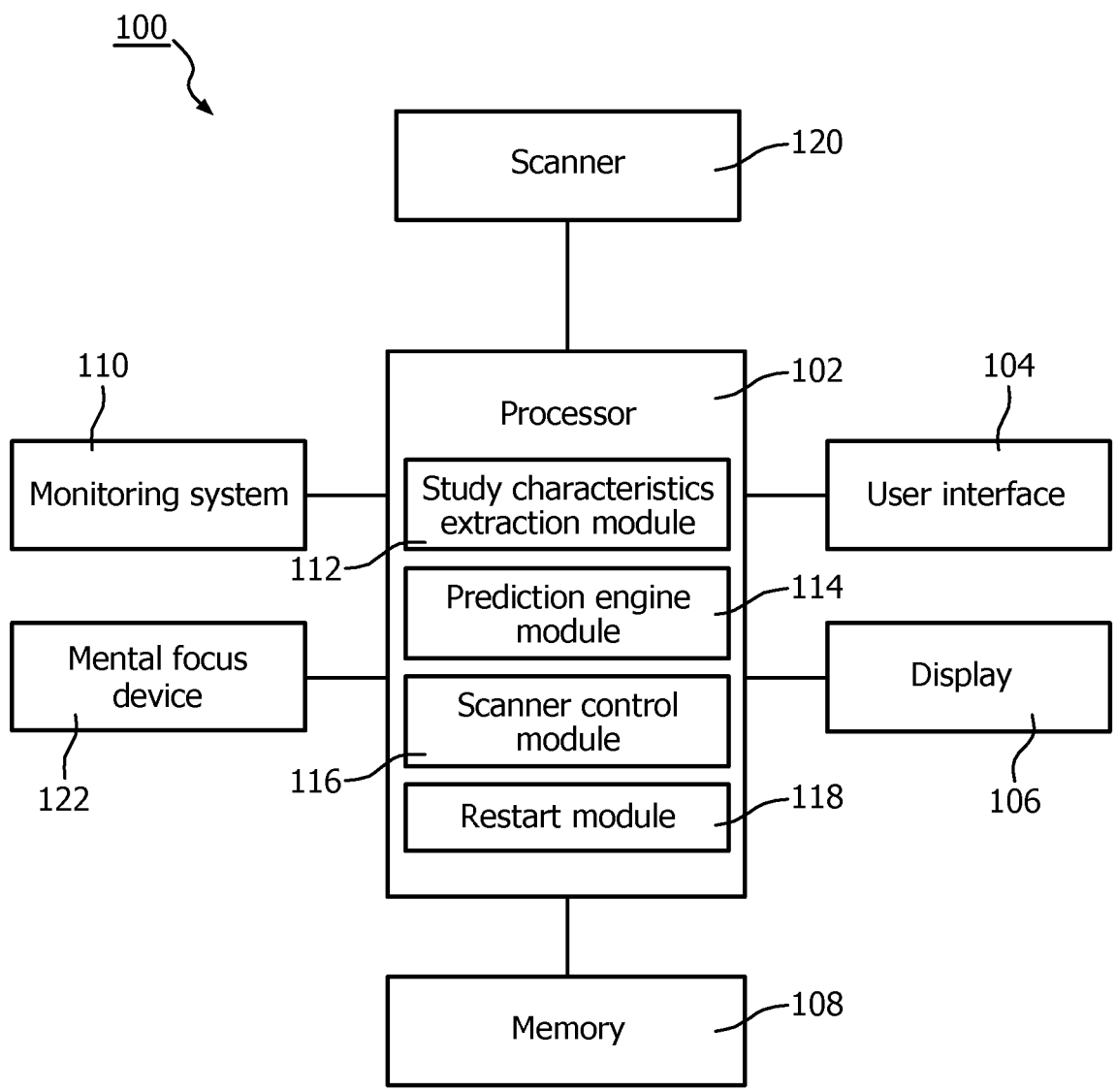
FIG. 1 shows a schematic drawing of a system according to an exemplary embodiment.

The exemplary embodiments may be further understood with reference to the following description and the appended drawings, wherein like elements are referred to with the same reference numerals. The exemplary embodiments relate to a system and method for optimizing a medical imaging process. In particular, the exemplary embodiments describe a system and method for predicting a motion of a patient and ceasing the acquisition of an image during the predicted motion period. Some patient motion may be voluntary such as, for example, when a patient moves to shift into a more comfortable position or to attend to an itch. Research has shown that neurophysiological measurements such as EEG, MEG or EMG show patterns can be used to predict and characterize the actual physical motion before the motion occurs. These measurements may correspond to the thought process that leads to the muscle contraction or the conveyance of that signal to the muscle groups that execute the voluntary motion. Involuntary motions may also be anticipated using similar approaches. Thus, by monitoring neurophysiological signals while a patient is being imaged, it is possible to predict some fraction of the patient motion that would adversely affect the imaging data and prevent the acquisition of image data during this period of motion.

Figure 2:
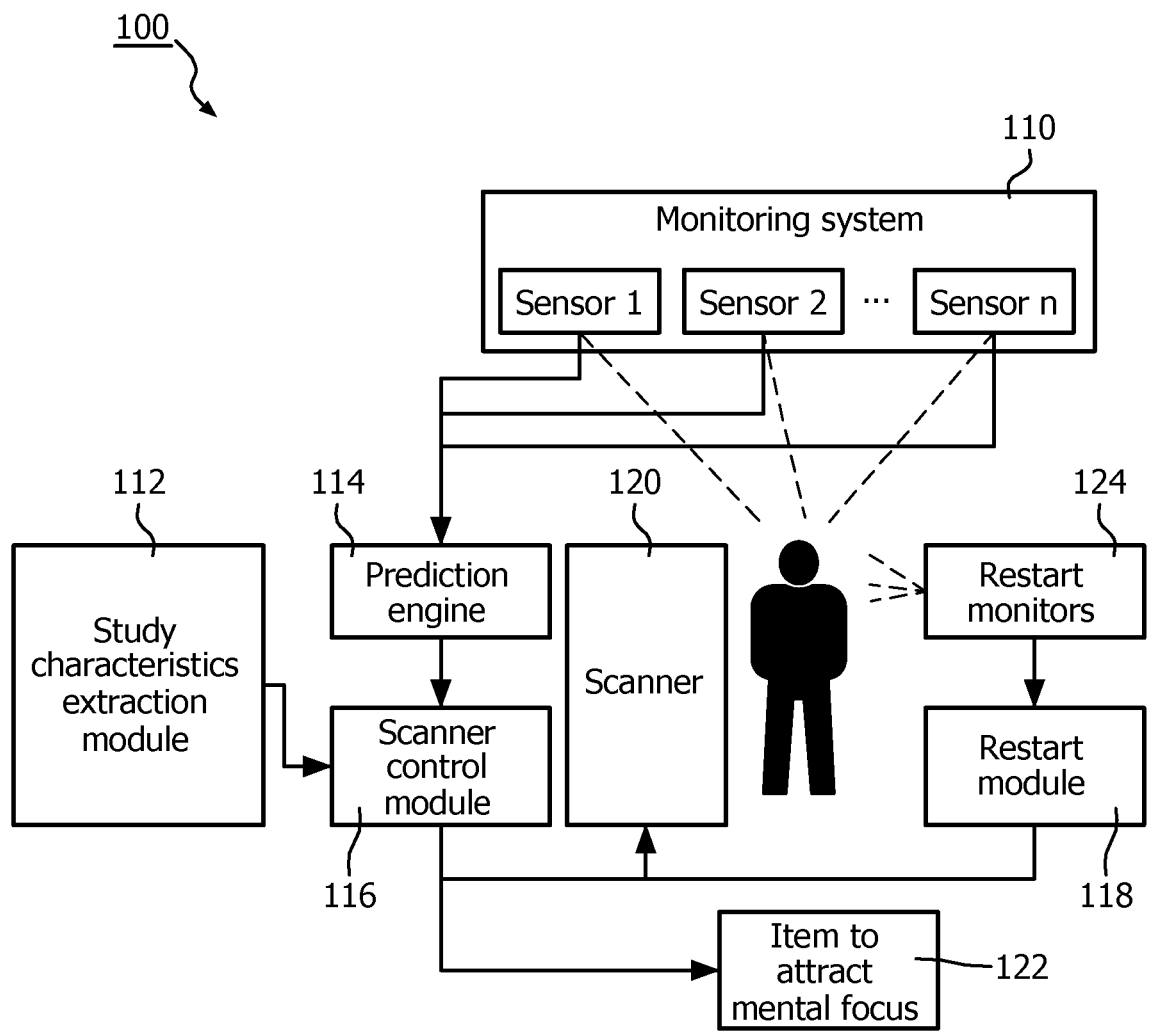
FIG. 2 shows another schematic drawing of the system of FIG. 1.

As shown in FIGS. 1 and 2, a system 100 according to an exemplary embodiment of the present disclosure predicts a motion of the patient during an imaging process via physiological measurements to avoid the acquisition of motion-corrupted data. The system 100 comprises a processor 102, a user interface 104, a display 106 and a memory 108. The processor 102 predicts the motion of the patient by measuring physiological signals from the patient via a monitoring system 110. The monitoring system 110 includes, for example, an electroencephalograph (EEG), a magnetoencephalograph (MEG), an electromyography (EMG), an electrocardiograph (ECG/EKG), a camera, a range imaging camera, a thermal probe or camera, pressure sensors or any sensor measuring any physiological state indicative of any upcoming motion, or any combination thereof. A study characteristic extraction module 112 extracts study information related to the requested image study such as, for example, body part (e.g., head, chest), modality (e.g., MRI, CT), protocol, resolution and view. A prediction engine 114 of the processor 102 interprets the signals measured by the monitoring system 110 and determines whether patient motion is likely to occur and the time at which the motion is likely to occur given the extracted study information. When the prediction engine 114 determines that patient motion will occur, the prediction engine 114 sends a stop signal to a scanner control module 116, which will cease the acquisition of image data by a scanner 120 during a given period. Optionally, the system 100 further comprises a restart module 118, which generates and sends a restart signal to the scanner 120 to restart the acquisition of image data. The restart signal is based on, for example, a manual intervention by the user and/or a sensor observation via a restart monitor 124 that indicates that the patient has returned to his or her original position. Alternatively, sensors of the monitoring system 110 are used to detect the return motion of the patient.

As an additional optional feature, the system 100 also further comprises a mental focus device 122, which attracts the mental focus of the patient to prevent the patient from moving. For example, if the patient focuses on the mental focus device, there is less likelihood that attention is directed on other things that may lead to patient motion. The mental focus device 122 is, for example, a light, a video on a screen, an audio signal, or anything else that can capture the attention of the senses of a human being. In this embodiment, the monitoring system 110 is be used to detect the patient's level of attention to the mental focus device 122. As image data is acquired, the data is stored in the memory 108. The memory 108 optionally also stores patient data such as patient information (e.g., identifying information, symptoms, diagnoses), prior scans and an exam order for the image scan. Once all of the image data has been acquired, as necessary, the processor 102 compiles the image data to generate a final image which may be displayed on the display 106 and/or stored to the memory 108. The user may indicate any desired preferences and/or settings via the user interface 104, which includes input devices such as, for example, a keyboard, a mouse and/or a touch display on the display 106.

Figure 3:
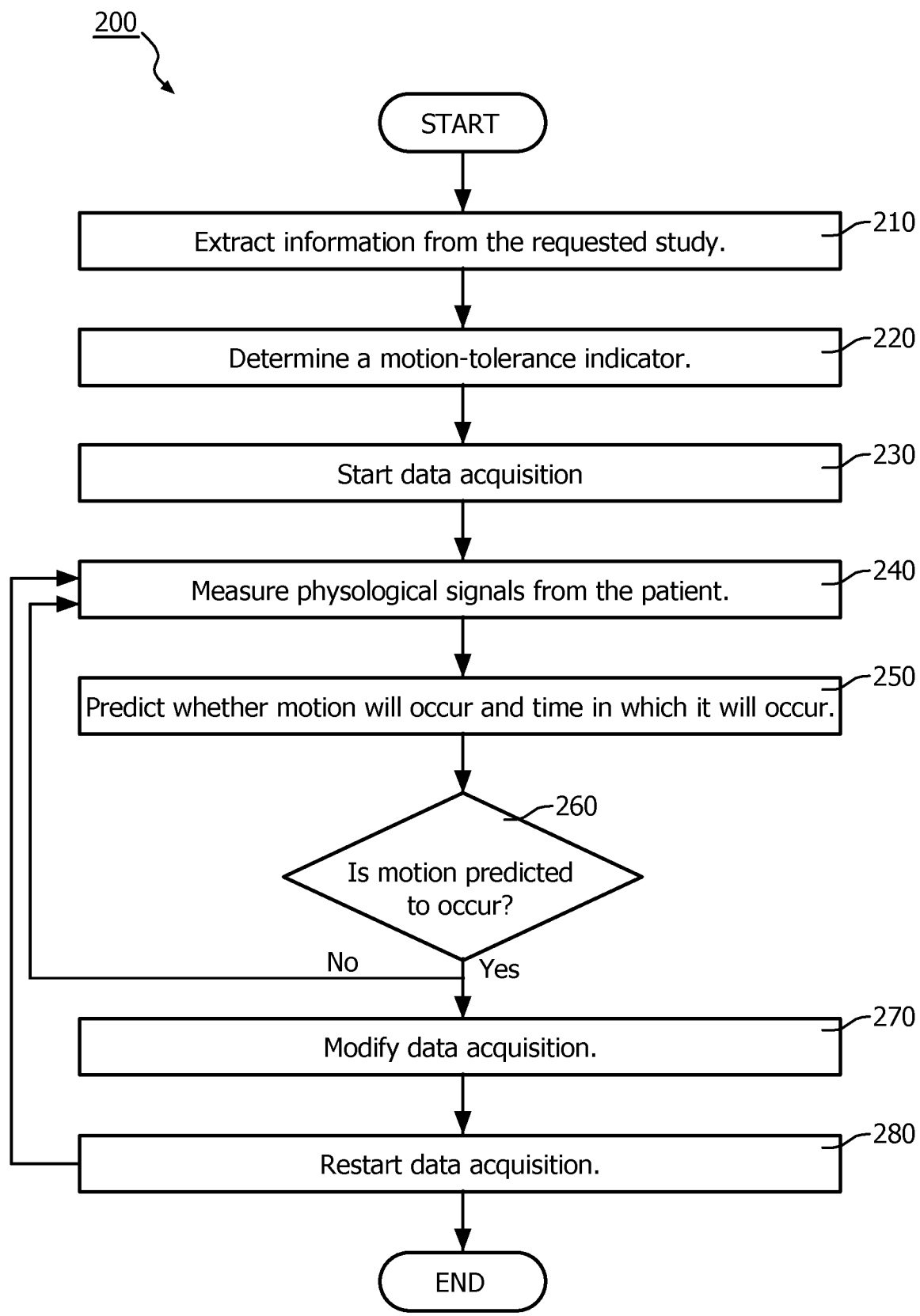
FIG. 3 shows a flow diagram of a method according to an exemplary embodiment.

FIG. 3 shows a method 200 by which the system 100 predicts the motion of the patient and prevents the acquisition of image data during this period. In a step 210, the study characteristics extraction module 112 extracts study information for the requested scan such as body part, modality, protocol, resolution and view. For example, the study characteristics extraction module 112 analyzes the exam order to extract the study information. The study information is then utilized to determine a motion-tolerance indicator, in a step 220. The motion-tolerance indicator is for example a threshold value or a range of values indicating a tolerated range of motion of the patient. The motion-tolerance indicator is determined via, for example, a look-up table by the type of exam (e.g., MRI, CT) to determine a range of motion that can be tolerated without negatively impacting the image reconstruction. For example, an MRI may have a shorter tolerance while a CT scan may have a longer tolerance.

In a step 230, the scanner 120 begins to acquire image data. Where the system also includes a mental focus device 122 such as, for example, a light, video on a screen, audio signal, etc., the mental focus device 122 is also activated so that the user focuses on the device 122 while the scanner 120 is acquiring data. Video signals such as interesting news can be used to attract the mental focus such that the patient may be prevented from moving. Before the start of the imaging exam, the patient may choose from a selection of video or audio themes so that the patient can stay as focused as possible during the imaging exam.

In a step 240, the monitoring system 110 measures physiological signals of the patient. The physiological signals include for example electromagnetic signals (e.g., brain waves or signals emitted from other nervous system elements), skin appearance (e.g., color, texture), temperature, respiration rate, heart rate, perspiration, conductivity or mechanical pressure, or camera-based face expression recognition indicative of unease. Where a mental focus device 122 is also being utilized, the monitoring system 110 can measure and detect the level of attention that the patient is focusing on the mental focus device 122. The higher the level of mental focus, the lower the likelihood that the patient will focus on other things such as, for example, itchy areas, thereby reducing the potential for body motion. This technique may also be used to detect how well the subject is focusing on instructions given by the imaging equipment operator. For example, for cardiac MR acquisitions, where several breath hold acquisitions are performed, the level of mental focus indicates the patient's mental cooperativeness to perform the commands to hold his/her breath.

In a step 250, the physiological signals are sent to the prediction engine 114 so that the prediction engine 114 can integrate these signals over time and/or across signal types into a prediction signal, which predicts whether patient motion is likely to occur and the time in which it will occur. In one exemplary embodiment, the physiological signals are integrated over time by averaging over a period preceding the instant of the prediction. Alternatively, the minimum, maximum, median, standard deviation or any other statistical measure may be used.

In one example of system operation, the physiological signals are integrated across signal types via a mathematical function such as a linear combination of the signal values generated by the monitoring system 110. Alternatively, the combination may be a nonlinear function, the properties of which may be determined through known machine learning or optimization methods. The prediction engine module 114 may be trained with data from prior patients. For example, a collection of training data may be obtained for which the signal values are known and the occurrence or non-occurrence of a subsequent patient motion event within a fixed or adaptive time frame are also known. The parameters of the mathematical combining function (e.g., coefficients, exponents, etc.) may be optimized such that the choice of those parameters leads to a prediction of the patient motion. Methods for defining and generating such a function include but are not limited to artificial neural networks, Bayesian estimators, support vector machine and nearest integer classifiers. These methods then produce a probability of a motion event occurring within the fixed or adaptive time frame. In a further embodiment, where a current patient has had repeated scans performed, the collected training data may be specific to the current patient. As a further option, the system 100 may further comprise a motion-detecting device such as, for example, a video camera with image analysis capability. The motion-detecting device is synchronized with the scanner 120. The prediction engine module 114 trained with data from prior patients is applied to the current patient to predict the motion of the current patient. If the current patient did not move as predicted, the recorded signals are labeled as belonging to the class of "no motion occurred." If the patient does move, the recorded signals are labeled "motion occurred." Once there is enough training data, the prediction engine module 114 is trained with the data of the current patient either alone or in addition to the training data of the prior patients to increase the performance and accuracy of the prediction engine module 114 in predicting the motion of the patient.

In another example of system operation, the prediction can be performed at one or more discrete time points and the generated predictions combined over time. If predictions are combined across signal types, the prediction engine module 114 may also predict the type of motion that is to occur. For example, the prediction engine module 114 may predict an anatomical location and scale of the predicted motion.

In a step 260, the scanner control module 116 receives the prediction signal and/or measured levels of attention to the mental focus device 122 to determine whether or not a motion is predicted to occur. For example, if the prediction signal exceeds a threshold value (e.g., the probability of motion is high) determined in the step 220, the system 100 may determine that a motion is predicted to occur and proceeds to a step 270, which modifies (e.g., ceases) the data acquisition. If the prediction signal is less than or equal to the threshold value, the system 100 may determine that a motion is not predicted to occur or is insufficient to impede the image reconstruction. In this case, the method 200 will return to the step 240 to continue to acquire physiological signals from the patient. As described above in regard to the step 220, the threshold value may vary based on extracted study information. The threshold value may vary depending on the body part. For example, the threshold may vary for scanning of the head compared with the chest compared with the legs. It will be understood by those of skill in the art that the determination of whether or not a motion—significant enough to affect image reconstruction—is likely to occur may be determined in any of a number of different ways using, for example, a range of values or a threshold value, as described above. Threshold values used to determine the level of the patient attention to the mental focus device may differ from the threshold values used to determine whether or not the data acquisition of the scanner 120 should be modified.

In the step 270, the data acquisition is modified when it is determined that the probability of motion exceeds a threshold value. In one example in which the scanner 120 is a CT scanner, the flow of electricity to the X-ray tube may be ceased when the motion is predicted to occur. In another example in which the scanner 120 is an MR scanner, the data acquisition may simply be ceased. In an alternative embodiment, if the movement location is predicted, then the acquisition may be shifted to a less motion sensitive area. For example, for MR scans in which image slices are obtained, the slice selection may be focused on a different part of the anatomy or portions of the MR k-space with less motion sensitivity closer to the center. In a further embodiment, the sensitivity of the system 100 may be adjusted by the user via the user interface 104. For example, the user may adjust the threshold value obtained in the step 220.

In a step 280, the restart module 118 sends a restart signal to the scanner 120 to resume the data acquisition or return to its original state. The restart signal may be based on a fixed timer, a manual intervention by the user or a sensor observation that indicates that the patient has returned to his/her original position. The sensors that detect this return motion may include elements of the monitoring system 100 or may be distinct. These sensors do not predict a motion but compare the current physical position of the patient with the physical position before the acquisition was modified in the step 270.

It is noted that the claims may include reference signs/numerals in accordance with PCT Rule 6.2(b). However, the present claims should not be considered to be limited to the exemplary embodiments corresponding to the reference signs/numerals.

Those skilled in the art will understand that the above-described exemplary embodiments may be implemented in any number of manners, including, as a separate software module, as a combination of hardware and software, etc. For example, the study characteristics extraction module 112, the prediction engine module 114, the scanner control module 116 and the restart module 118 may be programs containing lines of code that, when compiled, may be executed on a processor.

It will be apparent to those skilled in the art that various modifications may be made to the disclosed exemplary embodiments and methods and alternatives without departing from the spirit or scope of the disclosure. Thus, it is intended that the present disclosure cover the modifications and variations provided that they come within the scope of the appended claims and their equivalents.

What is claimed is:

1. A method for monitoring motion during medical imaging, comprising:
   initiating an acquisition of image data;
   measuring physiological signals of a patient, the physiological signals comprising at least one neurophysiological signal;
   predicting whether a patient motion will occur based at least in part on the at least one neurophysiological signal;
   modifying the acquisition of image data when it is predicted that the patient motion will occur;
   initiating a mental focus device attracting a focus of the patient; and
   detecting and measuring, via a sensor, the patient's level of attention to the mental focus device based on the patient's focus on the mental focus device wherein the measured level of attention is used to determine the patient's level of focus on instructions to modify the acquisition of image data for the patient based on the patient's level of focus on instructions by shifting the acquisition of data to a less motion sensitive area of the patient.

2. The method of claim 1, further comprising:
   extracting a study information for a requested medical image to determine a motion tolerance indicator indicating a tolerated range of motion of the patient.

3. The method of claim 2, wherein the study information includes one of body part, modality, protocol, resolution and view.

4. The method of claim 1, wherein the physiological signals are integrated over time by one of (i) averaging over a period preceding a prediction, (ii) determining a minimum, maximum or median, and (iii) calculating a standard deviation.

5. The method of claim 1, wherein the physiological signals are integrated across signal types via a mathematical function.

6. The method of claim 5, further comprising:
   a machine learning algorithm defining the mathematical function, wherein the machine learning algorithm is trained with one of (i) prior patient data including known signal values and occurrence or non-occurrence of subsequent patient motion within a fixed or adaptive time frame and (ii) current patient data acquired during previous imaging sessions, wherein the machine learning algorithm is at least one of an artificial neural network, a support vector machine, a Bayesian network, a decision tree, a linear discriminant and a nearest-neighbor classifier.

7. The method of claim 1, further comprising:
   generating a prediction signal by integrating the physiological signals, wherein determining whether patient motion is likely to occur includes determining whether the prediction signal exceeds a threshold value.

8. The method of claim 1, wherein modifying the acquisition of image data includes one of (i) ceasing the acquisition of image data, (ii) ceasing a flow of electricity to an x-ray tube.

9. The method of claim 1, further comprising:
restarting the acquisition of image data to an original state upon receipt of a restart signal, wherein the restart signal is based on one of a fixed timer, a manual intervention by a user and a sensor observation indicating that the patient has returned to an original position.

10. A system for monitoring motion during medical imaging, comprising:
a monitoring system measuring physiological signals of a patient, the physiological signals comprising at least one neurophysiological signal;
a processor initiating an acquisition of image data, predicting whether a patient motion will occur based at least in part on the at least one neurophysiological signal, and modifying the acquisition of image data when it is predicted that the patient motion will occur; and
a monitoring system for initiating a mental focus device attracting a focus of the patient and detecting and measuring, via a sensor, the patient's level of attention to the mental focus device based on the patient's focus on the mental focus device wherein the measured level of attention is used to determine the patient's level of focus on instructions to modify the acquisition of image data for the patient based on the patient's level of focus on instructions by shifting the acquisition of data to a less motion sensitive area of the patient.

11. The system of claim 10, wherein the processor extracts a study information for a requested medical image to determine a motion tolerance indicator indicating a tolerated range of motion of the patient.

12. The system of claim 10, wherein the processor generates a prediction signal by integrating the physiological signals and predicts whether the patient motion will occur by determining whether the prediction signal exceeds a threshold value.

13. A non-transitory computer-readable storage medium including a set of instructions executable by a processor, the set of instructions operable to:
initiate an acquisition of image data;
measure physiological signals of a patient, the physiological signals comprising at least one neurophysiological signal;
predict whether a patient motion will occur based at least in part on the at least one neurophysiological signal;
modify the acquisition of image data when it is predicted that the patient motion will occur;
initiate a mental focus device attracting a focus of the patient; and
detecting and measuring, via a sensor, the patient's level of attention to the mental focus device based on the patient's focus on the mental focus device wherein the measured level of attention is used to determine the patient's level of focus on instructions to modify the acquisition of image data for the patient based on the patient's level of focus on instructions by shifting the acquisition of data to a less motion sensitive area of the patient.

14. The method of claim 1, wherein the at least one neurophysiological signal is derived from at least one of an electroencephalograph (EEG), a magnetoencephalography (MEG) and an electromyograph (EMG).

15. The method of claim 1, wherein the predicted patient motion is non-cyclical.

* * * * *